United States Patent [19]

Hoefelmayr

[11] Patent Number: 5,746,153
[45] Date of Patent: May 5, 1998

[54] DEVICE FOR EXTRACTING FROM A MILKING FLOW AN ANALYSIS SAMPLE HAVING A PROPORTIONAL AMOUNT

[75] Inventor: Tilman Hoefelmayr, Niederteufen, Switzerland

[73] Assignee: Bio-Melktechnik Hoefelmayer & Co., Niederteufen, Switzerland

[21] Appl. No.: 575,516

[22] Filed: Dec. 20, 1995

Related U.S. Application Data

[62] Division of Ser. No. 303,867, Sep. 9, 1994, Pat. No. 5,645,012.

[30] Foreign Application Priority Data

Sep. 14, 1993 [DE] Germany ............ 43 31 203.9

[51] Int. Cl.⁶ ............................................. A01K 7/00
[52] U.S. Cl. ........................................... 119/14.01
[58] Field of Search .................... 119/14.01, 14.02, 119/14.08, 14.09

[56] References Cited

U.S. PATENT DOCUMENTS

| | | | |
|---|---|---|---|
| 3,308,669 | 3/1967 | Grise et al. | 73/422 |
| 3,599,607 | 8/1971 | Wallick | 119/14.17 |
| 4,016,832 | 4/1977 | Kiestra | 119/14.14 |
| 4,231,324 | 11/1980 | Schletter | 119/14.17 |
| 4,292,994 | 10/1981 | Johnson et al. | 137/351 |
| 4,452,176 | 6/1984 | Hoefelmayr et al. | 119/14.17 |
| 4,608,864 | 9/1986 | Savoyet | 73/202 |
| 5,116,119 | 5/1992 | Brayer | 356/28 |
| 5,388,549 | 2/1995 | Holroyd | 119/14.14 |

FOREIGN PATENT DOCUMENTS

| | | |
|---|---|---|
| 0 098 966 | 1/1984 | European Pat. Off. |
| 2 621 390 | 4/1989 | France |
| 3 118 865 | 12/1982 | Germany |
| 3 139 536 | 5/1983 | Germany |
| 3 210 465 | 9/1983 | Germany |
| 32 10 465 | 9/1983 | Germany |
| 3 214 734 | 10/1983 | Germany |
| 3 216 537 | 11/1983 | Germany |
| 32 16 537 | 11/1983 | Germany |

(List continued on next page.)

OTHER PUBLICATIONS

Pulsdauermodulierte Steuerung von Magnetventilen by H. Hesse and H. Möller. ölhydraulik und pneumatik 18, 1972, Nr. 11, pp. 451–457.

Primary Examiner—Thomas Price
Attorney, Agent, or Firm—Flynn, Thiel, Boutell & Tanis, P.C.

[57] ABSTRACT

A method and a device are presented with which an analysis sample of less than 50 ml can be extracted from a milk flow having an amount which is proportional, even for cows having an expected total milk amount of up to 30 kg as well as an expected maximum milk flow of 12 kg per minute. The method is characterized in that by using a valve controlled in cycles, whereby each cycle comprises a valve opening time and a valve closing time, for extracting simply an analysis sample held below a predetermined maximum amount of 50 ml from the expected value of the total milk amount to be milked from the particular cow gained from experience, a cycle time and a valve opening time are determined, whereby the cycle time and the valve opening time are respectively chosen in such a way that they lie within a predetermined range of values, that the valve opening time or the cycle time is controlled in dependence of the milk flow, and that to avoid the values of the valve opening time or the cycle time lying outwith the range of values as a result of a change in the milk flow, the valve opening time and the cycle time are changed in the same proportions to the values lying within the range. The device with which such a milk sample extraction can be carried out with, comprises a milk flow measuring device, a processor unit and a milk sample extracting device which substantially comprises an electrically controllable magnet coil with which a sealing body is moveable to a first position closing the through flow opening for the sample separating stream and a second position releasing this opening.

21 Claims, 9 Drawing Sheets

FOREIGN PATENT DOCUMENTS

| | | |
|---|---|---|
| 3 222 234 | 12/1983 | Germany . |
| 3 307 665 | 9/1984 | Germany . |
| 3 424 179 | 2/1985 | Germany . |
| 3 429 987 | 3/1985 | Germany . |
| 35 28 827 | 2/1987 | Germany . |
| 244 215 | 3/1987 | Germany . |
| 84 31 817.1 | 6/1988 | Germany . |
| 3 729 183 | 3/1989 | Germany . |
| 85 02 259 U | 4/1989 | Germany . |
| 3 942 606 | 6/1991 | Germany . |
| 906 460 | 2/1982 | U.S.S.R. . |
| 916 855 | 3/1982 | U.S.S.R. . |
| 1 099 907 | 6/1984 | U.S.S.R. . |
| 1 180 627 | 9/1985 | U.S.S.R. . |
| 2 069 726 | 8/1981 | United Kingdom . |
| 2 231 658 | 11/1990 | United Kingdom . |
| 82/04127 | 11/1982 | WIPO . |

DEVICE FOR EXTRACTING FROM A MILKING FLOW AN ANALYSIS SAMPLE HAVING A PROPORTIONAL AMOUNT

This is a division of Ser. No. 08/303 867, filed Sep. 9, 1994, now U.S. Pat. No. 5,645,012.

DESCRIPTION

The invention relates to a device for extracting from the milk flow milked from a cow, an analysis sample of an amount proportional to the milk amount which has been milked whereby, the sample partial amounts are extracted from the milk flow predetermined in dependence of the milk flow, as well as, a milk sample extracting device for carrying out this method having a milk flow measuring device disposed in a milking duct, and a processor unit for controlling the milk sample extracting device connected with an analysis sample container and which is in contact with the milk flow.

The quality of a milk and therefore the price paid per kg is directed towards its content substances, in particular, the percentage of fat content in the milk. The determination of the fat content is however, considerably made difficult when the milk has been standing a length of time since in this case the portion of fat preferably deposits on the upper surface of the milk. Therefore, there exists very tight regulations how to proceed with the extraction of a so-called representative analysis sample, which normally should not comprise of more than 50 ml. This method is extremely elaborate, labour intensive and also costs a lot in time.

A sample extracting device is already known from DE 35 28 82 7 with which the milk samples are extracted with the transfer of the milk delivered from the farm into a milk tank transporter. In this case, a so-called expected milk amount is adopted on the basis of the known delivered amount of milk of the previous days, and this amount of milk is respectively divided by an equal, predetermined number of extracting impulses. As a result, for every extracting impulse, a same amount of milk is apportioned which when multiplied with the number of impulses produces the expected total amount of milk. In dependence of the expected total amount, varying volume amounts can of course be asigned to each impulse. With the conveying of the milk, the milk volume measuring device is then set up in such a way that it outputs a respective impulse respectively after the calculated partial volume amount. With each impulse, a predeternmined, respectively equal sample partial amount is extracted from the milk. In this way, the total extracted sample amount, which is the product of the fixed number of impulses and the fixed sample partial amounts, is practically held constant.

On the other hand, Utility Model G 85 02 259.4 is concerned with a milk conveying device for a tank lorry or in-house milk transport operations in a dairy, where in a similar way, the number of constant sample partial amounts to be extracted is fixed by the amount of each sample partial amount to be extracted being laid down in relation to the total sample amount to be extracted and the time during which the sample partial amount is extracted. However, since with the transfer of the total milk amount differences in the total milk flow can arise, it has been suggested, to take into consideration the factor from the relation of the total milk amount to be transferred to the respective measured milk flow in order to correspondingly change the rest intervals between two partial sample extractions in dependence of the respective milk flow. The milk flow changes to be expected and, as a result, to be considered are however, relatively small.

It is known from DE 32 10 465 to extract from milk, proportional amounts from the milk flow which occurs directly during milking. In this case, in connection with a milk flow measuring device through which flows the milk which has been milked, a partial amount is respectively branched off with the help of a peristaltic pump, the running velocity of the peristaltic pump is controlled in dependence of the respective measured milk flow or the height level measured in the milk flow measuring sensor. Such an arrangement is however, only useful for a defined range of occuring milk flows, whereby, in particular, the peristaltic pump does not ensure anymore an exact sample extraction at high milk flows. Moreover, a peristaltic pump, especially with high running velocities, has only an extremely limited life expectancy and a relatively high energy consumption which is increased even more by the fact that the pump must work between vacuum and atmospheric pressure.

The same disadvantages apply to the arrangement known from DE 32 16 537 where a first peristaltic pump is used for measuring the milk flow while a second peristaltic pump serves to extract a sample. Added to the double energy consumption, is additionally the considerable weight of the total arrangement which excludes such an arrangement being used in a transportable hand device. Added to this, there occurs with such an arrangement, a relatively high so-called carry-over risk, due to milk remains remaining in the measuring device from the previous sample and which reach the subsequent measuring sample.

As already mentioned, so-called respresentative samples are mainly carried out with regard towards an exact determination of the fat content of the milk amount which has been milked. However, since with the standing of the milk, the fat has a tendency to deposit relatively quickly from the rest of the milk parts, an elaborate, long and exact method of procedure is required in order to extract a representative sample from the milk which has already been standing.

Such a method of course, would be unnecessary if it were possible to extract such a representative sample directly with the milking of the cow, that is, when the milk has not yet been standing. This method would also be desirable in view of the fact that each cow could be especially monitored and the milk content of the milk could be separately determined. However, the difficulty with such a method is based on the fact that despite considerable fluctuating total milk amounts per cow and despite strong differences in the milk flow and the time aspect during each milking from cow to cow, each time only a small analysis sample bottle of less than 50 ml content is made available into which a representative sample should be directly filled. The expected values of the total milk amount of a cow already differ between around 5 and 30 kg, that is, in a ratio 1:6 while the milk flows which can arise during a milking stage are between 0.1 and 12 kg per minute, that is, they can fluctuate with a ratio of 1:120. If one combines together both influence effects for the total milking amount and the milk flows, there arises a possible broad range of possible changes to be expected in a ratio of 1:720. If one considers at the same time the task that the amount of the analysis sample can only fluctuate between 20 and 40 ml, that is, at the most in a ratio of 1:2, this even results in a range of variations to be covered, which, when the main influence factors are taken into consideration is of 1:360.

Up till now, with the contemplated pumps these problems cannot be solved. A peristaltic pump which conveys a predetermined volume through the pinching of a tube, cannot be controlled over a region of 1:360 since its maximum range of speed amounts merely to 1:100 and in this case an expensive equal current control is necessary. In particular, there is as well the control of the required equal current motor in the lower speed region, which is very problematic. Apart from this, a peristaltic pump of this type is not be very well suited for a transportable measuring device to be used with a cow since, apart from a relatively energy consumption, it requires a large weight and also a large construction volume. Added to this, the life expectancy of the required tube is small since the elasticity of this tube changes with time whereby at the same time the transported volume is changed.

In the same way, an electro magnetic pump which operates with a membrane is not able to cover the required region of 1:360. As well, it is necessary to connect valves with such a pump through which the problem of a sufficient cleaning is present, since in operation the milk tends to stick to or collect on the valve, that is, there arises an increased danger of curdling. Finally, such electromagnet pumps also have a relatively high current consumption.

The present invention therefore strives to obtain a method, as well as, a device, with which a representative analysis sample of less than 50 ml can be taken separately for each cow, during the milking.

This is achieved by a method according to the invention of the type mentioned above, in that by using a valve controlled in cycles, whereby every cycle comprises a valve opening time and a valve closing time, for extracting simply an analysis sample held under a predetermined maximum amount of 50 ml from the expected value of the total milk amount to be milked from the particular cow gained by experience, a cycle time and a valve opening time are determined whereby the cycle time and the valve opening time are respectively chosen in such a way that they lie with a predetermined range of values, that the valve opening time or the cycle time is controlled dependent on the milk flow, and that to avoid the values of the valve opening time or the cycle time lying outside the range of values as a result of a change in the milk flow, the valve opening time and the cycle time are changed in the same ratio to the values lying within the range of values.

With such a method, representative analysis samples can be extracted from a large fluctuating range of the total milk amount to be expected which is between 5 and 30 kg as well as a possible milk flow between 0.1 and 12 kg per minute.

For making the method easier, the separated sample partial amounts are held under the same pressure as the milk flow itself.

For simplifying the control, the milk reservoir height is preferably held constant above the valve for producing a separating flow substantially independent from the milk flow.

On the other hand, the measurement region can still be extended when the method is carried out in such a way that a milk reservoir height dependent respectively on the milk flow is produced above the valve for changing the separating flow through the valve dependent on of the milk flow.

The range of values for the cycle time within which the cycle time is changeable, is determined at its lower boundary practically only by the controllability of the reproduceable milk separating amount of the valve and at the other end by the number of the samples to be extracted with small milk flows for producing a representative sample, and lies preferably between 0.5 and 30 seconds (120 to 2 cycles per minute). Preferably the range of values lie however, between 2 and 30 seconds.

The range of values for the valve opening time is determined with small opening time significantly by the inertia of the valve and with the upper opening times which means up to those opening times which with a constant milk flow, a constant separating flow is achievable. In that case, the range of values lies between 0.05 and 1.2 seconds with high milk flows and respectively preferably, between 0.1 and 0.8 seconds and can be reduced with very small milk flows to the range of 0.1 to 0.25 seconds.

As is known, the fat content of the milk being milked increases toward the end of milking. As a result , also the viscosity and the flow behaviour of the milk slightly changes. In this connection, the influence of capillary forces can also be of significance. For these reasons, it an be useful for fine calibrating the fat content contained in the analysis sample with a progressive reduction in the milk flow towards the end of milking, to progressively somewhat increase or decrease the valve opening time.

Preferably, the method is carried out such that during each closing of the valve, a part of the milk which has flowed through the valve is pumped back and preferably, the method is further carried out in such a way that with every opening of the valve a suction force is exerted on the milk for accelerating the start of the milk flow.

The invention also concerns a milk sample extracting device for carrying out the method having a milk flow measuring device disposed in a milk duct, a processor unit for controlling the milk sample extracting device connected with an analysis sample container and is in contact with the milk flow, and is characterized in that the milk sample extracting device comprises an electrically controllable magnet coil with which a sealing body is moveable to a first position closing a through flow opening for the sample extracting flow, and a second position in which this opening is released.

Preferably, this sealing body is made out of a permanent magnet or a ferromagnetic material and near to the through flow opening, a body made out of a ferromagnetic material or a permanent magnet is disposed holding the sealing body in its first position. This embodiment allows an energy saving operation since a simple change over impulse of a short duration is necessary in order to move the sealing body from its first postion to its second position and vice-versa. This can be carried out by respective short impulses of around an impulse duration of 10 to 100 ms, which respectively lead a current of opposing direction one after the other. The change-over in the current direction can, for instance, be carried out in that merely the voltage at the ends of the magnetic coil is reversed in polarity which can be carried out with the help of electronic controls.

In practice, it has proven to be especially useful that the sealing body is made out of a cylindrical body which is guided in lateral guides. The body and respectively, the guides should preferably be made out of such material, or be provided with a covering of such material, that produces a small a friction as possible between the guides and the body.

It is useful, when a pipe which determines the through flow opening for the sample extracting stream forms the ferromagnetic body or the body formed out of a permanent magnet.

For optimal seal-proofing and also for reducing the noise of operation and for extending the lifetime, the sealing body and/or the end of the through flow opening facing the sealing body, is provided with a layer of absorbing or damping material. Such a damping material can be formed, for instance, in the form of a plate out of e.g. silicon or polyurethane or however, can also be made in the shape of a steel spring wire, which is covered with silicon.

To enhance the safety of operation and the operation preciseness, the magnetic coil is disposed with the height of the second position of the sealing body.

In order to facilitate a faultless discharge of a milk amount, separated for the sample extraction under equal pressure a particular duct is provided which, on the one hand, is connected with the milking vacuum and on the other hand, is led to the end of the milk sample extracting device. This discharges the air from the analysis bottle which is driven out by the filling of the milk. In this way, it is guaranteed that as well as above the milk flow, from which a milk sample should be separated, the same pressure, namely, the milking vacuum in the above case, also prevails at the outlet end of the milk sample extracting device.

In order to keep the threat of carry-over through the milk sample extracting device as small as possible, on the one hand, the spaces provided for the milk through flow are as small as possible, however, on the other hand, are also so formed that the milk can easily discharge and also allow the milk sample extracting device to be cleaned as well as possible. An arrangement which has shown to be advantageous is where the cylinder shaped sealing body is moveable along a substantially cylindrical formed guide way, and in whose surfaces, facing the sealing body, recesses are provided extending in the longitudinal direction of the sealing body which are in contact with the through flow opening in the second position of the sealing body and in contact with the end of milk sample extracting device which faces the analysis sample holder.

To achieve a faultless functioning of the valve, in particular, with small valve opening times, as well as also to prevent the blocking, in particular, the curdling of the through flow opening, it is useful, to affect the embodiment in such a way that the connection between the through flow opening and the recesses for drawing of the milk is substantially interrupted with an adjustable movement of the sealing body over a predetermined distance (D) before reaching the closing position of the through flow opening and respectively, during the opening movement of the sealing body.

According to a preferred embodiment, the milk sample extracting device is directly connected with a chamber in which is set up a milk built-up or reservoir, corresponding to the respective milk flow. This chamber is preferably a corresponding chamber of the related milk flow measuring sensor. For measuring the reservoir height, also additional devices could be provided in this chamber, for instance, measurement probes disposed along the height at a distance from each other.

A reduced expense in calculation and control is then required when, according to a further embodiment, the milk sample extracting device opens up into a chamber in which the milk flow is respectively held at a predetermined reservoir height. This can, for example, be achieved by a corresponding connection with a milk flow measuring device accordingly constructed, and actually can be achieved in a so-called sump region.

With the above-described embodiment, while a separation in accordance with the hydrostatic pressure is being carried out, a separation can also be achieved according to another embodiment in that the through flow opening of the milk flow sample extracting device is connected with a sample extracting pipe projecting into a milk transporting duct. In this case, a dynamic sample extracting is carried out In this case, it has proven to be useful, to arrange the sample extracting pipe such that the longitudinal axis of its inlet opening is disposed from the inside wall of the milk transporting duct at around a distance of a third of the diameter of the milk transporting duct.

According to a preferred embodiment of the dynamic sample extractor, the sample extracting pipe branches off in a first duct connected with a discharge conductor in the analysis sample holder and which also surrounds the outlet opening, and a second duct which is connected with the milk flow, whereby the sealing, body is moveable in such a way that it closes the outlet opening in its first position and releases the second duct and in its second position releases the outlet opening and the first duct and closes the second duct.

In the following, the invention is further explained with the help of the embodiments represented in the drawings.

Figure 1:
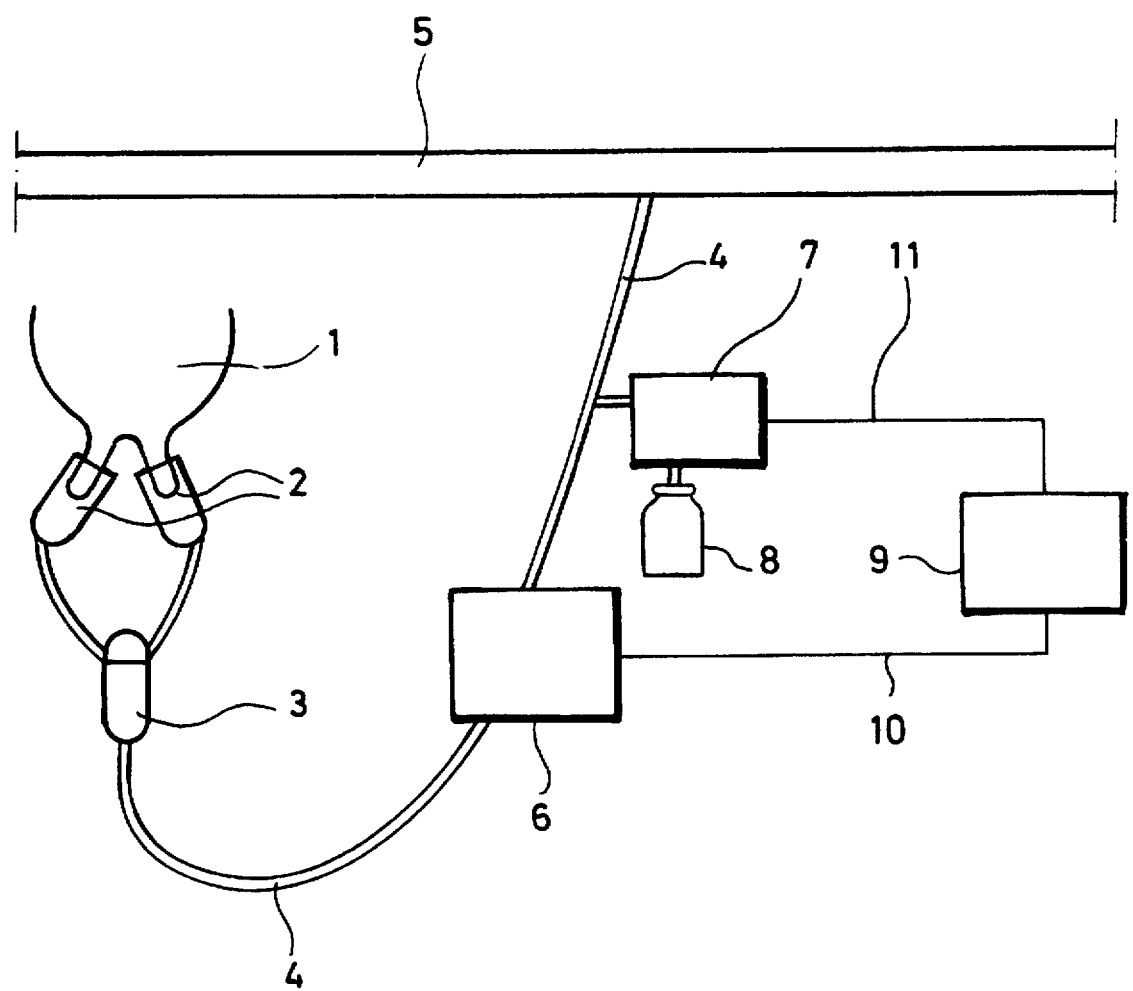
FIG. 1 shows a schematic representation of a milking arrangement employing the method and the milk sample extracting device according to the invention.

In FIG. 1, the udder 1 of the cow is schematically represented on whose teats milking cups 2 are placed. The milk milked with these milking cups is brought together in a so-called milk collection piece 3 in a single transport duct 4 which transfers the milk to a total transporting duct 5 which, for example, is guided overhead and is kept under the milking vacuum. In the long milking tube 4 a milk flow measuring device 6 is disposed. Furthermore, a milk sample extracting device 7 is shown which is connected with the long milking tube 4 or, in such cases, with the milk flow measuring device 6 and which collects the extracted sample in an analysis sample bottle 8. A processor 9 in which determined allowed values can be inputted receives over the conductor 10 signals from the milk flow measuring device 6 corresponding to the milk flow and the height of the milk reservoir in the milk flow measuring device, calculates in such situations a flowed volume of milk or a change in the milk flow per unit of time, as well as, valve opening times and cycle times, and controls via conductor 11 the milk sample extracting device 7.

Figure 2:
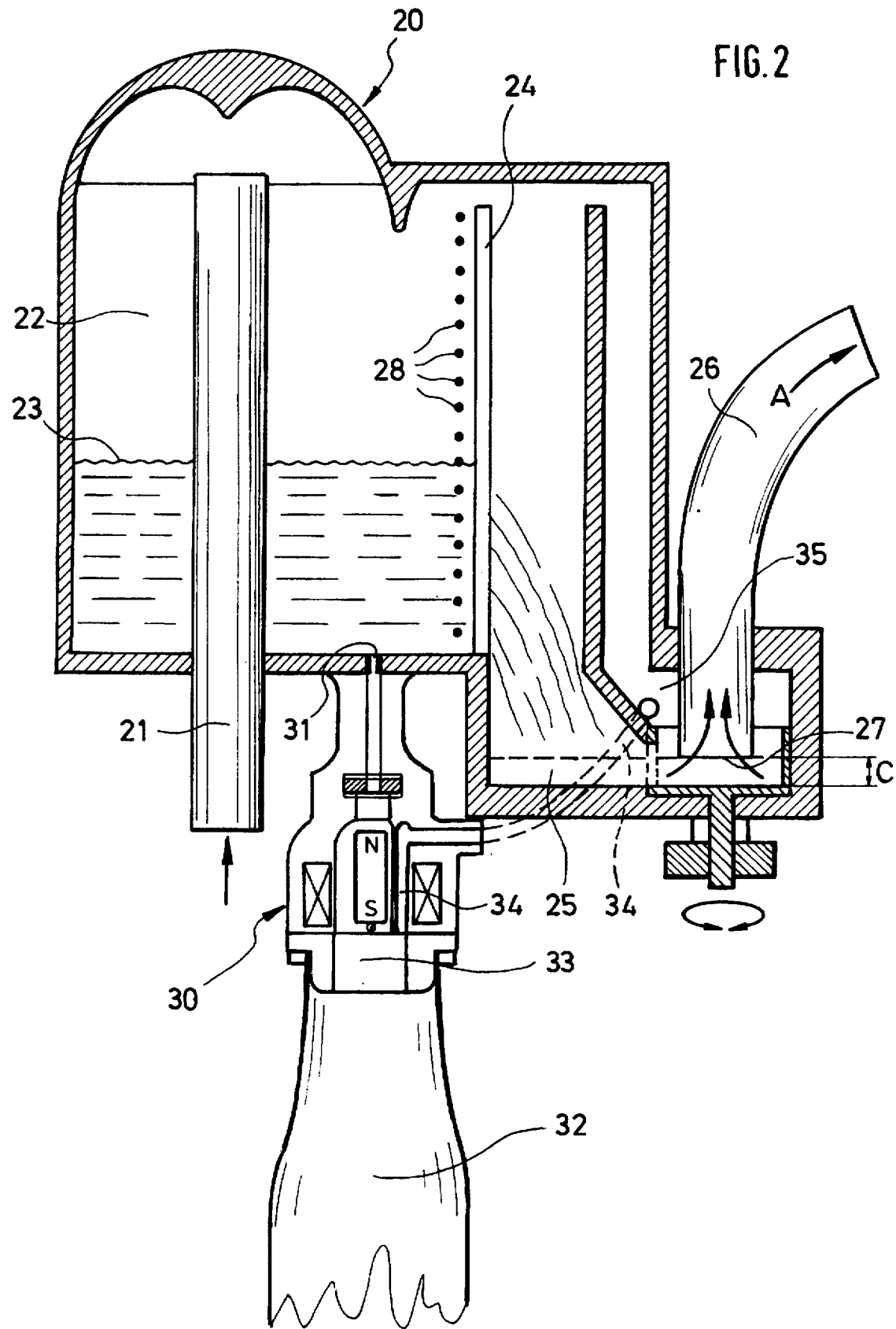
FIG. 2 show s a schematic representation of a section of a milk flow measuring device as well a milk sample extracting device according to the invention.

FIG. 2 shows a universal milk flow measuring device indicated with reference number 20. Via a pipe 21 which can be a part of the long, milk tube 4, under the presence of a milking vacuum the milk reaches upwards into the measuring and collecting chamber 22. Corresponding, with the respective milk flow, the milk builds-up in the chamber up to a reservoir height 23. The milk which has built up in the chamber 22 flows from the measuring and collecting chamber over a measuring slit 24 into a so-called sump 25. In this sump 25, a milk outlet duct 26 protrudes from above which likewise can be a part of the long milk tube. By way of the outlet duct 26, the milk in the sump 25 up to the height of the lower end 27 of the outlet conductor is sucked away on the basis of the milking vacuum effective therein. Therefore, in this sump part 25 the milk has a respective constant height C.

In the measurement and collecting chamber 22, a plurality of reservoir sensors 28, are disposed in front of the measuring slit 24 respectively along its length at a distance from one another, with which the milk reservoir in this chamber can be established. For the continual or cyclic scanning of these reservoir sensors 28, a separate electric scanning device, not shown, can alone be provided in the milk flow measuring device 20, by means of which a single signal corresponding to the height of the reservoir can then be transmitted to the processor 9. An appropriate scanning device for the reservoir sensors can of course also be provided in the processor 9 which scans the individual reservoir sensors via the conductor 10 and forms alone in the processor a corresponding reservoir height signal.

A milk sample extracting device 30 has a hollow housing and is provided underneath the milk flow sensor 20 which is connected thereto via a calibrated opening 31 in the bottom of the measuring and collecting chamber 22. Different embodiments of this milk sample extracting device 30 is to be described later with the help of FIGS. 6 to 10.

An analysis sample bottle 32 is fixed to the lower end of the milk sample extracting device 30 in which is filled the extracted sample. The lower end 33 of the milk sample extracting device projecting into the analysis sample bottle 32 is connected via a conductor 34 connected to this end with the space 35 above the milk sample. In this part of the milk flow measuring device the milking vacuum prevails.

Figure 3:
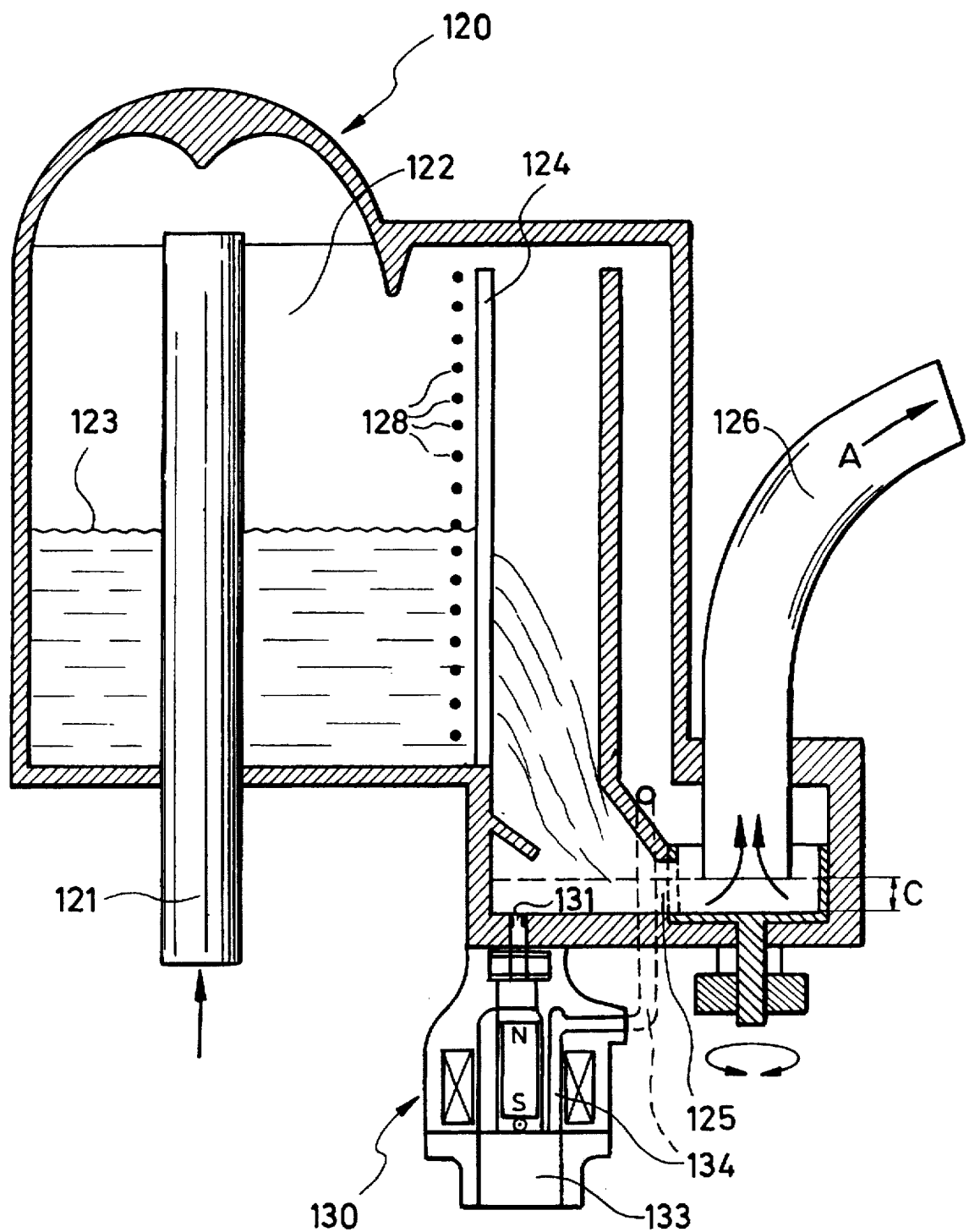
FIG. 3 shows a schematic representation of a section of a milk flow measuring device having a milk sample extracting device according to another arrangement of the invention.

FIG. 3 shows a milk flow measuring device as well as a milk sample extracting device of the same type as in FIG. 2 whereby the same parts are identified with the same reference numbers only that they have been increased by the factor 100. This embodiment differentiates itself solely from the embodiment shown in FIG. 2 in that the feeding line to the milk sample extracting device is provided via a calibrated opening 131 in the bottom of the housing of the milk flow measuring device in the region of the so-called sump 125. In contrast to the embodiment shown in FIG. 2, the height of the milk reservoir in the region of the sump stays at the constant height C independent from the respective existing total milk flow.

With the above described embodiments, the milk sample extracting device is shown in combination with a respective milk flow measuring device. Instead of the milk flow measuring device as shown, of course other types of milk flow measuring devices can also be employed which have a different working principle, for example, milk piston analysing type of milk flow measuring device or deposit working type of milk flow measuring device. A coupling of the milk flow measuring device and the milk sample extracting device is of course not necessary however, it does contribute to a compact form of the whole device. Of course, the milk sample extracting device can also be connected with the separate space to which the milk flows while it builds up to a predetermined height corresponding to the respective milk flow or, the extracting device can also be connected with a space in the duct transporting the milk in which the milk is held constant at a predetermined height by way of the milk sample extracting device.

Figure 4:
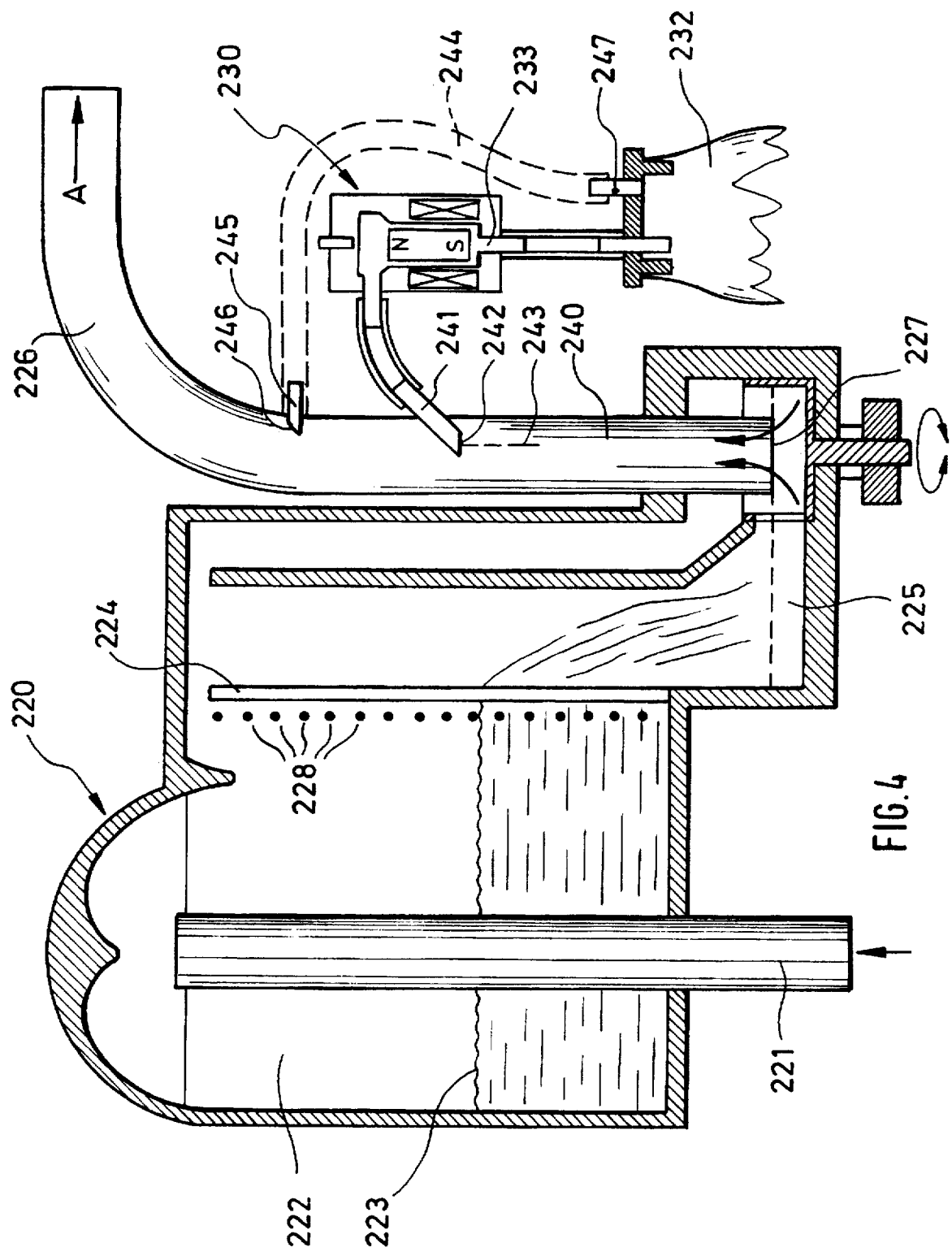
FIG. 4 shows a schematic representation of a section of a milk flow measuring device to which is connected a milk sample extracting device according to another arrangement of the invention.

With the above embodiments of the milk sample extracting device, the hydrostatic pressure produced by the built-up milk plays a respective role for the separating flow which flows into the respective analysing sample bottle. On the other hand, with the following two embodiments to be described, a milk separation takes place with the help of the kinetic energy of the milk flow accelerated once again from a milk sump. In FIG. 4, the same components are identified with the same reference numbers as in FIG. 2, but have been increased by a factor of 200. The milk is transported from the milk flow measuring device 220 by the way of the outlet duct 226 in the direction of the arrow A. A small extracting pipe 241 projects into the vertical extending part 240 of the outlet duct 226 whose free opening 242 directed downwards has a free cross-sectional area which is around the factor 50-100 or even less in proportion to the free cross-sectional area of the outlet duct 226. Since the milk pistons or piston-like stoppers being transported in the outlet duct 226 do not always have a uniform form and, for example, they can be formed quite longer at the inner side of the duct 226 than in the middle of the conductor pipe, in order to reach from each piston a possible exact proportional amount of separation of milk, the middle 243 of the free opening 242 is so disposed that from viewing it lies from the inside wall of the outlet duct 226 at a distance of a third of the inside diameter when one assumes a somewhat circular shaped cross-section for the outlet duct as also for the free end 242. Were it the case that the milk sample extracting device 230 is continually opened, the milk flow flowing into the analysing sample bottle would be dependent on the milk flow and, as well, closely reproducable but the amount of milk flow would not be proportional. In order to make the amount of milk flow proportional, the milk flow must be controlled with a valve according to a corresponding characteristic curve. However, for the dividing-off or separating of a sample amount of less than 50 ml, small pipe cross-sections must be used so that the measurement would be extremely inaccurate and, for another, insurmountable cleaning problems would occur.

That also with this system, the separating of the milk is carried out under equal pressure, the analysis sample bottle 232 is still connected with the milking vacuum via the duct 244 shown only with a dashed line and via the pipe 245 projecting in the inside of the outlet duct 226. In order to prevent milk reaching into the analysis sample bottle despite the fact that the opening 246 of the pipe faces away from the milk flow, an extremely small bore 247 of, at the most, 0.5 to 0.8 mm in diametre is provided in the duct 244. The opening is so dimensioned that a light stream of air takes place from the bore 247 through the duct 244 and into the inside of the outlet duct 226, in order that the penetration of milk in the duct 244 is from the outset prevented. On the other hand, the opening 247 should also be so small that practically no loss of vacuum occurs in the duct 244 since the inside of the analysis sample bottle 232 should be held at the milking vacuum. This opening is preferably attached at the start of the duct 244 near to the pipe 245.

Figure 5:
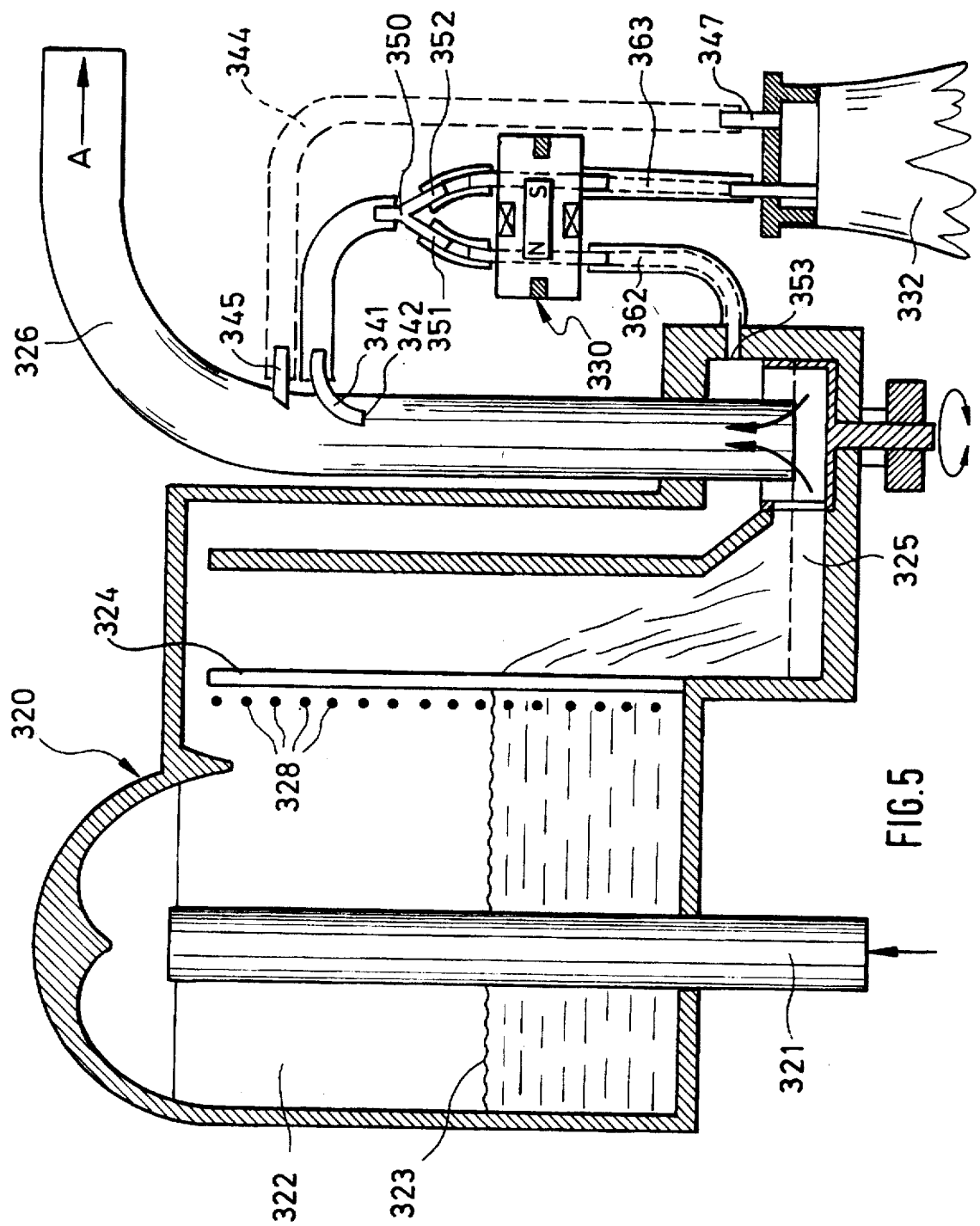
FIG. 5 shows a schematic representation of a section of a milk flow measuring device combined with a schematically represented further embodiment of a milk sample extracting device according to the invention.

FIG. 5 shows a modified embodiment of the milk sample extracting device with respect to the milk sample extracting device shown in FIG. 4. The remaining same parts are identified with the same reference numbers but are increased by a factor 300. These parts will not again be discussed in detail.

The pipe 341 projecting in the outlet duct 326 is divided into two ducts 351 and 352, by way of a branching 350 from which the duct 351 is connected with the milk sump 325 of the milk flow measuring device 320 via the milk sample extracting device 330 and the end 353 of the duct 351. The other duct 352 is connected with the analysis sample bottle 332 via the milk sample extracting device 330. The milk sample extracting device 330 comprises a reversing valve as shown in individual detail with the help of FIG. 10.

Figure 6:
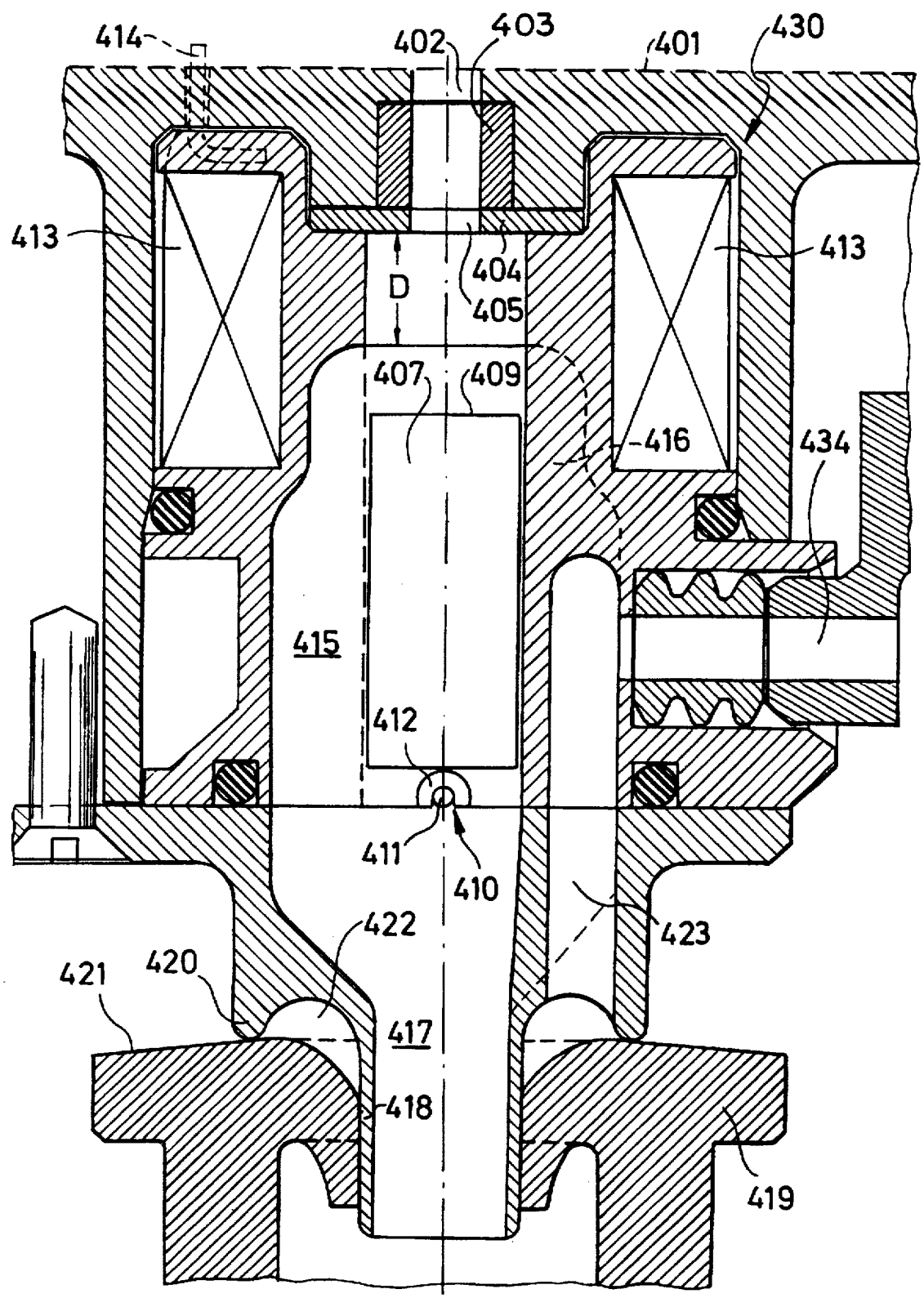
FIG. 6 shows an enlarged longitudinal cut-away view through a further embodiment of a milk sample extracting device according to the invention.

FIG. 6 shows an embodiment of a milk sample extracting device which may be related to those embodiments of FIGS. 2, 3 and 4. The milk sample extracting device has a hollow housing 430 which is attachable to the underside of the milk flow measuring device 20 in such a way that the upper side 401 lies against the underside of the milk flow housing and the calibrated opening 31 is aligned with the passage opening 402. The lower part of the passage opening 402 is configured by means of a ring-shaped body 403 which is either made out of a permanent magnetic or out of a ferromagnetic material. A deflector plate 404 lies against the underside of the body 403 made from a shock-absorbing material such as silicon or polyurethane. For the case where the other conditions remain unchanged, the adhesive force of the permanent magnetic can be exactly adjusted by way of the thickness of this plate. The deflector plate has an opening 405 aligned with the passage 402 and is at least of the same size. Instead of the deflector plate 404, an absorbing layer can also be provided which is directly fixed to the underside of the body 403. A substantially cylindrical hollow cavity 406 may be provided below the deflector plate 404, having a height D and a diameter greater than the diameter of opening of 405. This height D is shorter than the total valve lift. The diameter is somewhat greater than the moving sealing part. This produces the piston effect of the valve which will be described below in more detail. In the hollow cavity, a body is guided which moves in a vertical direction. The body 407 is preferably a circular cylindrical body however, another shaped body which is moveable in the hollow cavity 406 can also be provided so long as it simply has a top surface 409 which can, in a first upper position, lie leak-proof against the deflector plate 404 in order to tightly seal the passage 402. As shown in FIG. 6, the sealing body 407 rests in its second lower position on a buffer 410 which, for instance, is made out of a steel wire 411 which extends transverse to the cylindrical hollow cavity 406 and has a covering 412, for instance, made out of a silicon material, for absorbing any movement. The sealing body 407 is preferably made out of a permanent magnetic material.

A magnetic coil 413 is disposed coaxial to the axis of the cylindrical hollow cavity 406 which can be loaded via an electrical lead 414.

Recesses 415 and 416 (FIG. 6) are provided in the side walls of the cylindrical hollow cavity 406 underneath the height D which, in the second lower position of the sealing body 407 shown in FIG. 6, are in contact with the inner space 406 of the cylindrical hollow cavity and are in contact at the lower end with a discharge duct 417. The discharge duct is formed at its lower end in the shape of a hollow piercing needle 418 which, for instance, can pierce the vent plug 419 of an analysis sample tube not shown in detail. A ring-shaped projection 420 is formed coaxial to the hollow piercing needle 418 which comes to a sealing arrangement against the upper side 421 of the vent plug 419. In this way, a circular space 422 is formed between this ring-shaped projection 420 and the vent plug which connects with a duct 434 via a recess 423. This duct 434 can be the duct 34 shown in FIG. 2 or the duct 134 shown in FIG. 3 which is connected with the milking vacuum. In this way after piercing the end 418 in the vent plug 419, a milking vacuum is present in the circular space 422 which, on the one hand, prevents that a pressure increase is produced in the analysis sample bottle by way of the sealing of the plus 419 and that, on the other side, also that the volume of gas in the inside of the analysis sample bottle which is suppressed by the incoming milk, can be evacuated so that it is garanteed that a sample extraction can take place under equal pressure.

In such situations which require it, the valve can also be formed, for instance, as a pinch valve, by which, for instance, a tube is pinched or respectively released.

Figure 7:
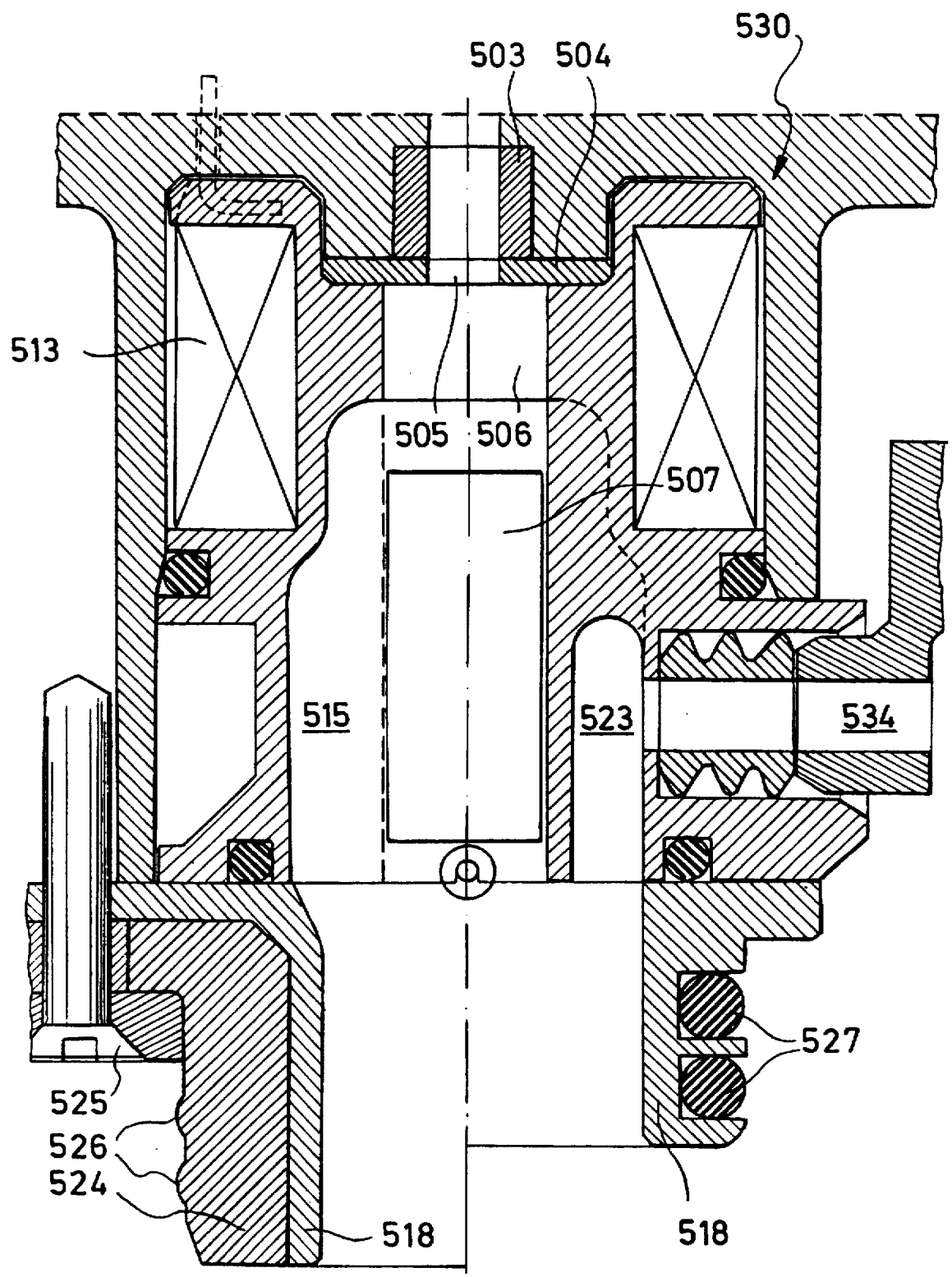
FIG. 7 shows an enlarged cut-away view of a milk sample extracting device according to the invention similar to the embodiment shown in FIG. 6 whereby simply two different fixing means for an analysis sample bottle are represented.

A similar embodiment of a milk extracting device is shown in FIG. 7 whereby the same parts are identified with the same reference numbers but are increased around the factor 100. In this figure, a further embodiment is shown merely in the lower left half in which a stopper 524 is placed on the lower end 518 of the pipe and can be fixed to the housing 530 with a screw 525. On to this stopper 524, a corresponding pipe-shaped analysis sample container can then be place whose inner circumference then lies sealed against the extensions 526.

Another embodiment is shown in the lower right half of FIG. 7 with which two O-shaped sealings rings 527 are supported on the outer side of the pipe 518 upon which an analysis sample container can than be directly pushed on in a seal-proof manner.

Figure 8:
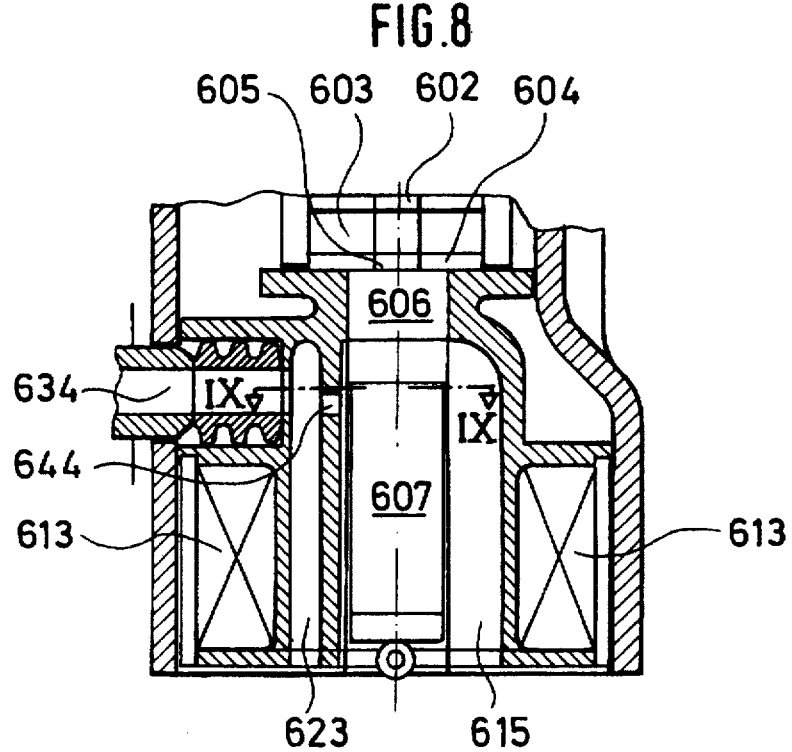
FIG. 8 shows a sectional view of a further embodiment of a milk sample extracting device formed according to the invention.
Figure 9:
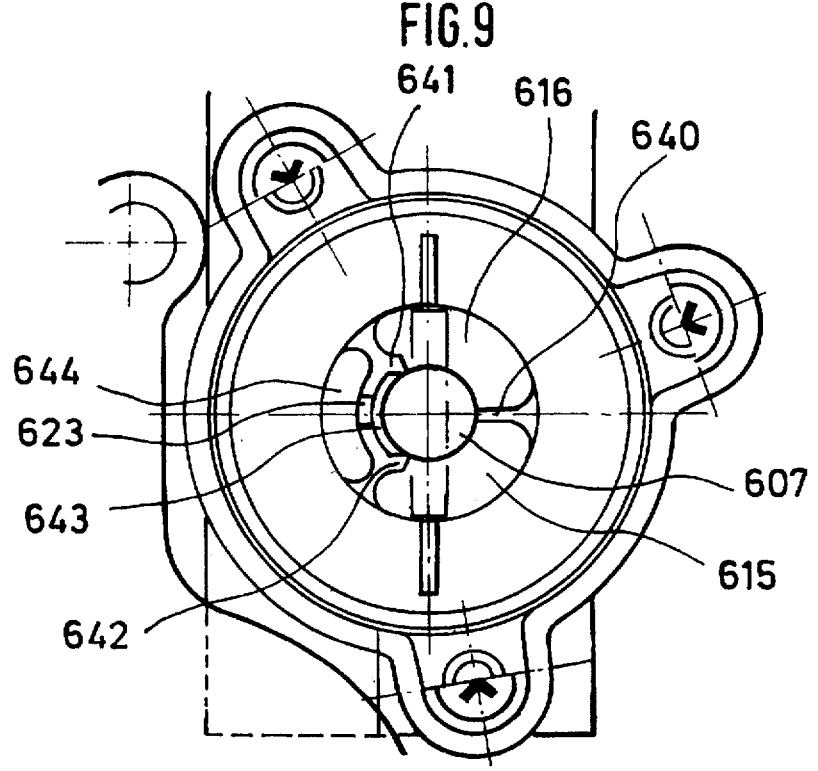
FIG. 9 shows a section along the line IX—IX of the embodiment shown in FIG. 8.

FIGS. 8 and 9 show a further embodiment of a milk sample extracting device which is a simple modification of the milk sample extracting device corresponding to FIG. 6 whereby the same components are identified with the same reference numbers as in FIG. 6 but have been increased by the factor 200. With this embodiment, the magnet coil 613 is displaced to the lower end of the sealing body 607 to be found in a second lower position, which has proven to be an extremely stable support for an exact closing and opening function of the sealing body. Here, the sealing body is simply guided on three guide ridges 640, 641 and 642. Between the ridge 640 and the ridges 641 and 642, the recesses 615 and 616, already described, are respectively provided for the outlet of the milk. Additionally, on the other hand, a flat recess 643 is formed in between the ridges 641 and 642 which are connected with the chamber 623 via a further recess 644 and which is held under milking vacuum. The recess 644 has the effect that the upper end of the sealing body 607 is also under vacuum in the second lower opening position so that a frictionless discharge of the milk is achieved (no pipette effect).

The separating of the milk with the milk sample extracting device described in FIGS. 2 to 4 and 6 to 9, is preferably carried out in such a way that the arrangement functions as an open-closing-valve. Starting from the second lower position of the sealing body 407 shown in FIG. 6, should, for instance, an electric impulse having the right direction of current and strength be given to the magnet coil 413, the sealing body 407 is moved upwards until it comes to position against the defector plate 404. In this first upper position, the simultaneous closing position corresponds to the interruption of the flow of milk through the duct 402 by the sealing body 407. Since, either the sealing body 407 or the ring 403 is made of a permanent magnet while the respective other piece is made out of ferromagnetic material, the sealing body 407 is held in this position also when the magnet coil 413 does not carry any more current. The opening of the valve requires simply a somewhat same size of impulse with an opposing current direction to be sent through the magnet coil 413 in order to overcome the magnetic adhesive force between the ring 403 and the sealing body 407 and to bring the sealing body back again to its second lower opening position. In this position, the milk flow is released through the duct 402. In this second lower position, there is likewise no need of an adhesive force of the magnetic coil for the sealing body 407 since this body rests on the buffer 410. Since the sealing body can be made from an extremely small body of merely around 6 mm diameter and around 16 mm length, which has a lift of around 8 mmn, while the duct 402 at the closing end has a diametre of around between 1.5 and 3 mm, the inertia mass of the sealing body 407 can be held extremely low since the total volume of the sealing body lies under 1.35 ml and under a weight of 10 g. Therefore, it requires simply the smallest impulse of 10 to 100 ms in length which has a maximum power of around 1.5 Watt in order to open or close the valve. This means that alone with a very high operating cycle the medium energy consumption is extremely low (typically 0.2 Watt) since no energy is consumed between the impulses. However, of more significance is still the fact that with such a valve, defined opening times down to 0.05 second opening time with a designed separating flow are obtainable.

For controlling the valve, the impulses are preferably fed to the magnet coil having opposed direction of current so that the voltage at the magnetic coil is pole reversed. According to a useful embodiment, the arrangement could be made so that instead of one magnet coil, two magnet coils are provided which are wound in opposite directions whereby the impulse is alternatively fed to the first and respectively the second magnet coil in order to move the sealing body from the first to its second position and back.

Although the above apparatus has been described preferably in connection with an impulse control, nevertheless, the apparatus could be carried out without the use of a permanent magnet and simply by using a ferromagnetic material for the sealing body in such a way that a current in a first direction is fed respectively to the magnet coil which flows as long as the the time the sealing body is to be held in one of its positions. For moving the sealing body in its other position, the direction of current is then reversed and the current preferably held in turn so long until a change-over takes place. Such a procedure would however, significantly increase the current consumption and the heat load of the coil.

With the embodiment shown in FIG. 6, a certain piston effect is produced during movement of the sealing body over the distance D. Such a piston effect is not absolutely necessary for the working of the valve however, it has proven extremely advantageous.

The result of the piston effect which can be built into the valve is as follows:

with the closing of the sealing body, its top surface travels piston-like a length D in the cylindrical shaped hollow cavity 406. Along with it the milk found in this cylinder cavity is displaced with the effect that the separating or dividing canal 402 is from backwards blown free as a result of which the milk for the next following separating cycle is optimally exchanged. This additionally improves the representative sample. As well, this free blowing due to the piston effect, causes a cleaning of the complete separating canal including apertures 31, 131 from eventual dust particles before every separating cycle. In the cleaning stage of the device, this effect can be still further increased and made of further use by a greatly increased valve switching frequency (for example 90–120 S/min).

With the opening movement of the sealing body following the closing movement, milk is sucked from the separating canal by way of the same piston effect before the milk flows freels away at the end of the cylinder length D by way of the top surface of the sealing body through the recesses 415, 416 to the analysis bottle. The volume of milk which is sucked in with the opening of the valve and respectively pushed back with the closing thereof, is of the same amount and has therefore no (direct) influence on the separating amount. This forward and backward pushing of the volume of milk is dependent simply on the effective length of the cylinder section D and in such cases, also on the circular gap between piston and cylinder. As well, the total lift of the sealing body must be considerably greater than length D since only so that the milk can finally flow out via the recesses. On the basis of the small dimensions of the cylinder (eg. diametre 6 mm length D 5 mm). The capillary and cohesion forces of the milk act so strongly that the cylinder in a vertical position before the next closing stage is always filled with milk. Should the accelerating movement of the sealing body vary with opening and with closing this can be corrected by setting up a varying current strength to the coil(s) for the two directions of movement.

The most important advantage of the described piston effect is however, the following:

for the realization of a sample whose amount is proportional everytime and a carry-over error which is as small as possible as well as a reservoir height which is also as small as possible, the separating canal above the through flow opening 405 of the valve should be as short as possible. With this, there is produced, in particular, with low milk flows, very small hydrostatic pressures (typically 0.5 to 2 cm head of water). Also, the build-up pressures with kinetic separating systems (see, for instance, FIG. 4 and 5) are very small with low milk flows. With such low hydrostatic and respectively hydrodynamic pressures, the capillary, cohesion and wall forces of the milk come in useful. The result is an irregular, imprecise and sluggish starting of the separating stream after the release of the outlet opening 405 of a conventional opening-closing, valve (without the piston effect). The described piston effect acts here specifically as an aid for overcoming the sluggish, imprecise starting action of the separating stream with very low hydrostatic and respectively hydrodynamic pressures. First, in this way, short and very short valve opening times per cycle for the smallest but reproduceable separating amounts are made possible, just as they are inevitably necessary for a representative sample with low milk flows, which should be directly filled in a small analysis bottle.

With increasing hydrostatic and respectively build-up pressures, the separating flow starts every time spontaneously and directly such that the piston effect automatically runs more and more in emptiness because the separating flow of the piston movement follows easily and without resistance. Correspondingly, the natural leakage is disturbed in a small way at high pressures.

The exact leakage proportions under the inclusion of the given piston effect are best determined empirically. Along with this, for instance, in the laboratory, the possibility is set up for the adjustment of a concrete device arrangement for varying levels of hydrostatic or hydrodynamic pressures (eg. 0.5, 1.0, 2.0, 4.0, 8.0 cm head of water) and respectively, for corresponding milk flows (eg. 0.1, 0.25, 0.5, 1.0, 2.5, 5.0, 9.0, 12.0, L/min). The separated amounts are detected for each level, produced with varying combinations of valve opening time per separating cycle and the number of separating cycles. At the same time it is important that the product of the valve opening time and cycle time per minute, that is, the opening time (S/min) is held constant which means that the theoretical separating amount for the respective level is respectively constant.

Empirically, it emerged however, that the actual separated amounts within the individual levels are not always the same amount. In particular with low pressure and respectively low flow levels produces varying combinations of control factors, valve opening time/cycle and number of cycles/min variations, that is, not the constant separating amounts as expected, even when the opening time is always held strictly constant. Therefore, at the respective same level with short valve opening times (with corresponding higher number of cycle/min), a greater separating amount is reached than with longer valve opening times (with corresponding smaller number of cycles/min). This result obviously connects with the fact that with increasing cycle number/min (with corresponding decreasing valve opening time) likewise, the more often the piston effect is effective which lends a simple acceleration help to the sluggish starting of the separating flow with each valve opening at low levels. To present these relationships as a characteristic diagram (separation amount; valve opening time; pressure and respectively flow level), therefore shows that with low levels (eg. milk flow 250 ml/min) in the range between e.g. 0.1 and 0.25 s valve opening time, the separating amount is practically constant and has a very good reproduceability. With increasing longer valve opening times per separating cycle (with corresponding smaller separating cycles) however, the separating amount reduces progressively in its size. Under these conditions, the frequency of the piston effect does not suffice anymore in order to guarantee a reproduceable stable separating stream. The problem of the starting of the separating flow on the basis of its inertia progressively reduces with increasing higher milk flows and respectively pressure so that finally within the high levels, all technically possible combinations of valve opening times and number of cycles/min produces a constant and very reproduceable separating amount which corresponds to the theoretical calculation. Therefore, from this viewpoint, with the high levels it is not necessary anymore to restrict the region for the valve control factors.

In reference to the frequency of a closing and opening movement, it has been established that 120 cycles per minute having a defined opening time and closing time, which together produce the cycle time, are absolutely realizable for a defined separating flow. A high cycle number of this type has however the disadvantge that an increased wear sets in and in this connection, the produced noise level is proportionally high. It is therefore preferred that the valve is operated with a low cycle number per time, for example, under 30 cycles per minute.

In order to obtain a sample which is as representative as possible and has no carry-over under all the milk flow conditions, it should be seen to that the volume of the feed-line 402 is as small as possible and is held at around the same magnitude as the separated milk amount per opening or, that in the volume 402, a constant milk exchange corresponding to the total milk flow takes place. In this connection, the milk sample extracting device possesses the significant advantage that on the basis that the shortest possible opening times of the cross-section of the feed line 402 can be chosen proportionally large so that proportionally large separating flows are possible and that nevertheless a representative sample can be obtained since with every opening and closing step the milk from the line 402 is pumped back and newly or freshly sucked in so that respective fresh milk is separated from the respective milk flow.

Figure 10:
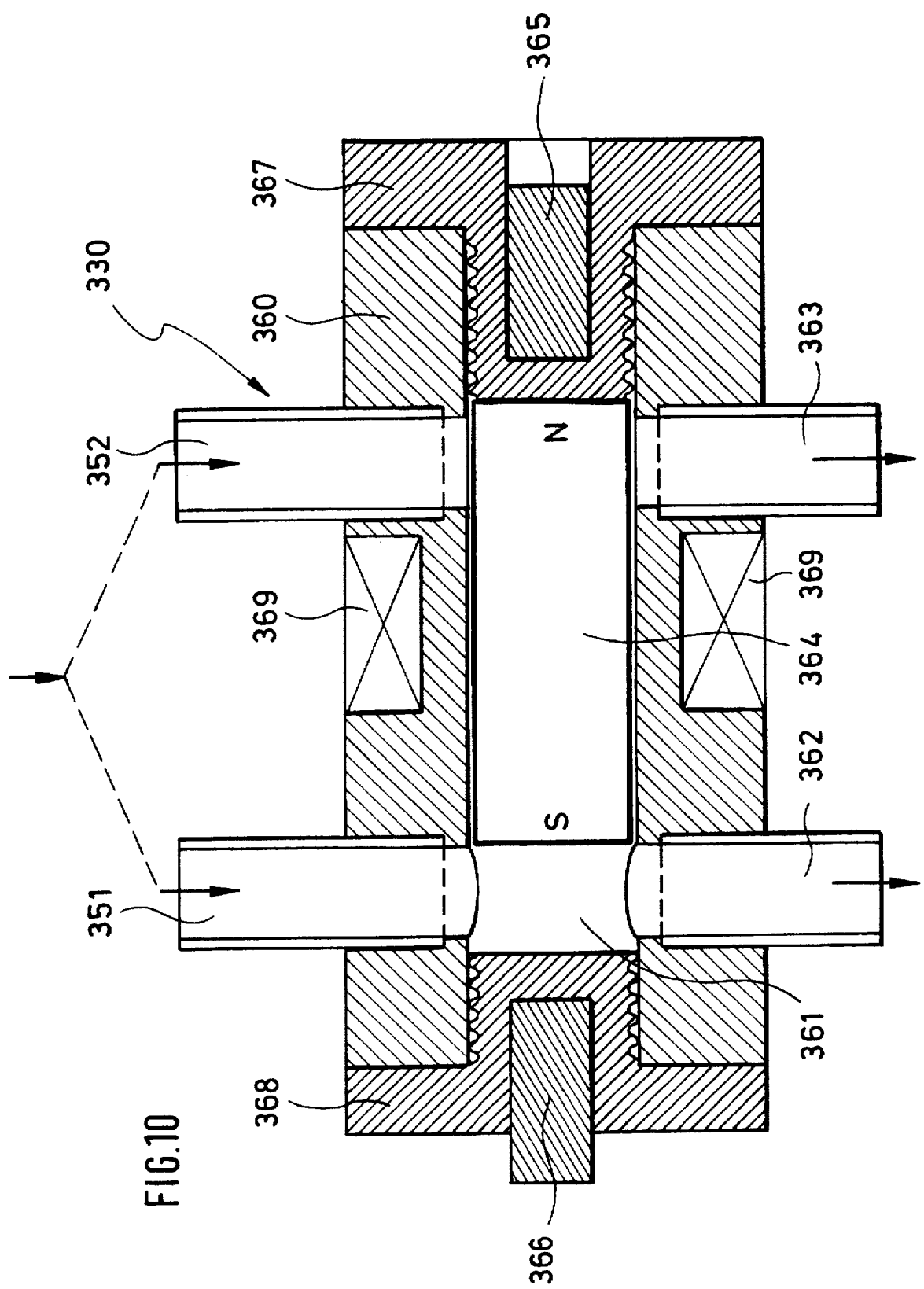
FIG. 10 shows a section of the milk sample extracting device shown in FIG. 5.

FIG. 10 shows in individual detail the milk sample extracting device schematically shown in FIG. 5. The ducts 351 and 352 open into a substantially cylindrical hollow cavity 361 formed in the housing. On the side walls of the hollow cavity opposing the openings of the ducts 351 and 352, outlet ducts 362, 363 aligned with the first mentions ducts are provided. In the hollow cavity 361, a cylindrical permanent magnet 364 is likewise provided comprising a substantially same cross-section surface as the hollow cavity 361. The permanent magnet is displaceable in the hollow cavity 361 along it axis between a first position shown in FIG. 10 in which its right end seals the ends of the ducts 352 and 363 and releases the ends of the ducts 351 and 362, and a second position not shown in FIG. 10, in which its left end in FIG. 10 seals the ends of the ducts 351 and 362 while it releases the ends of the ducts 352 and 363. In the housing 360, two ferromagnetic bodies 365 and 366 are disposed on the axis of the cylindrical permanent magnetic 364, respectively at a distance to its first and respectively second position. The known bodies are each held in a plug shaped part 367 and respectively 368 and are each made out of a material which dampens the movement of the core. With the movement of the permanent magnet 364 from it first position to its second position and back, the magnet comes into respective arrangement against these plug-shaped parts. An electromagnetic coil 369 is disposed coaxial to the axis of the permanent magnet 364. With the help of preferably impulse shaped currents of a corresponding size which are sent through the electromagnetic coill 369, the electromagnet can be moved from its first position to its second position and from its second back to its first position through which the permanent magnetic is then held through respective magnetic forces on the ferromagnetic bodies 366 and 365 without the further flow of current through the electromagnetic coil.

The milk sample extracting device shown in FIG. 10 in connection with FIG. 5, has the advantage that from the respective milk stream a portion is continually separated which flows back in the milk sump 325 through the branching 350 and the ducts 351 and 362 when the permanent magnet 364 is located in the position shown in FIG. 10. This milk stream is interrupted when the permanent magnet is moved to its second position while a milk sample separating stream can then flow through the ducts 352 and 363 into the analysis sample container. By holding the volume of the branching 350 and the ducts 351 and 352 as small as possible, it is insured that in the duct 351 leading to the hollow cavity 361, milk is practically always found corresponding to the respective milk flow whereby a presentative sample extraction is insured and starting problems of the separating stream at low build-up pressures do not arise.

For carrying out the method according to the invention using a milk sample extracting device and respectively a valve of the above-described type, the following, observations and determinations are assumed:

a) In the analysis sample holder, a respective amount of milk of between 20 to 40 ml should be separated independent from the expected value E, that is, the total milk amount in kg (or respectively in ml) of the cow to be milked. For the observations, a separated total sample volume of 30 ml is therefore assumed.

b) Furthermore, the separated partial amounts should be taken proportional to the respective milk flow.

Under these assumptions, it follows that, in dependence of the milk flow a

Separation volume/time (ml/min) = (1)

$$\frac{\text{Total sample (ml)}}{\text{Expected value (ml)}} \times \text{Milk flow (ml/min)}$$

must be separated in order to arrive at the total sample amount.

From now on if one determines the separating flow (ml/min) with a continually opened valve=the separated flow 100%, for instance, according the arrangements of FIGS. 2 and 3, so is it established that the separating flow 100% (for a continually opened valve) flows out through the bottom opening 31 and respectively 131 having a determined cross-section (A), a function of the build-up or reservoir height H (and respectively the hydrostatic pressure) is according to the following formula:

Separating flow (100%) [ml/min]=60×μ×A×SQR(2×g×h)  (2)

whereby:

g=acceleration due to gravity (cm/S²)

h=reservoir height (cm)

A=cross-section of the bottom opening (aperture) (cm²)

μ=outflow correction value 0.63

SQR=square root

When the reservoir height H, that is, the hydrostatic pressure with a changed milk flow, does not change, the value of the separating flow (100%) is constant. This results e.g. for a constant reservoir height of H=2 cm and an aperture diametre of 0.15 cm from which the cross-section of the bottom opening A=0.0176 cm², there follows a constant separating flow (100%)=41.67 ml/min.

Should the size of the milk flow be measured in a reservoir container via the reservoir height (and respectively the hydrostatic pressure) before a vertical extending, measurement slit of constant width S (for instance, as in the embodiment shown in FIG. 2), then arises the following relationship:

Milk flow (ml/min)=60×μ×S×⅔×SQR[2×g]×h^(3/2)  (3)

whereby:

g=acceleration due to gravity (cm/s²)

h=reservoir height (cm)

S=slit width (constant) (cm)

μ=outflow correction value 0.63

SQR=Square root

In connection with the equation (2), the separating flow (100%) dependent on the milk flow can be determined as:

Separating flow (100%)

60×μ×A×SQR(2×g)×[(milk flow)/<60×μ×S×⅔×SQR(2×g)>]^(1/3)  (4)

For a slit width of S=0.25 cm, for example taking to be constant, and an aperture cross-section of A=0.0176 cm²

(=1.5 mm aperture diametre), the following theoretical of values is calculated therefrom:

TABLE 1

| Measured milk flow (ml/min) | Separating flow (100%) (Valve constantly open) (ml/min) |
|---|---|
| 100 | 20,93 |
| 250 | 28,41 |
| 500 | 35,78 |
| 1000 | 45,07 |
| 2500 | 61,15 |
| 5000 | 77,03 |
| 9000 | 93,68 |
| 12000 | 101,95 |

Of course, a table of this type can also be represented as an empirically measured characteristic curve. This table allows, from now on, the necessary opening times of the valve in seconds/minutes to be determined in order to obtain the separating volume/time in ml/min inputted at the beginning:

$$\text{opening time (s/min)} = \frac{(\text{separating volume (ml/min)} \times 60\ s)}{(\text{separating flow } 100\%)(\text{ml/min})} \quad (5)$$

It would follow therefrom, according to Table 2, a necessary opening time in (with a constant reservoir height).

TABLE 2

(necessary opening time in sec/min for constant reservoir height)

| Milk flow | Expected amount: | | |
|---|---|---|---|
| (ml/min) | 30,000 ml | 10,000 ml | 6,000 ml |
| 100 | 0,14 | 0,43 | 0,72 |
| 2500 | 3,60 | 10,79 | 17,99 |
| 12000 | 17,28 | 51,84 | 86,39 |

From this, results in a relationship of maximum: minimum opening time of 86.39: 0.14=617:1.

Since values greater than 60 s/min are not possible, this would mean that the constant separated flow (here 41.67 ml/min) must have been increased around at least the factor 1.5 in order to arrive at realistic opening times. From this, the shortest opening time would however fall below 0.1 s/min which would cause individual valve opening times per cycle of much less than 0.1 seconds, and as a result, it would be technically difficult to realize.

With varying reservoir heights, on the other hand, would result in the following necessary opening times in s/min:

TABLE 3

(necessary opening time in sec/min with varying reservoir heights)

| Milk flow | Expected amount: | | |
|---|---|---|---|
| (ml/min) | 30,000 ml | 10,000 ml | 6,000 ml |
| 100 | 0,29 | 0,86 | 1,43 |
| 250 | 0,53 | 1,58 | 2,64 |
| 500 | 0,84 | 2,52 | 4,19 |
| 1000 | 1,33 | 3,99 | 6,66 |
| 2500 | 2,45 | 7,36 | 12,26 |
| 5000 | 3,89 | 11,68 | 19,47 |
| 9000 | 5,76 | 17,29 | 28,82 |
| 12000 | 7,06 | 21,19 | 35,31 |

From this a relationship of maximum: minimum opening time of 35.31: 0.29=122:1 would follow.

Should one want to proceed according to these theoretical opening times, then the difficulty exists in that it results in relatively long opening times, for instance, with high milk flows and low expected amounts, during which of course the milk flow can already have seriously changed, such that no representative sample would be extracted. On the other hand, with low milk flows and high expected values, there is produced a very short opening time during which it is not really certain that the assumed proportionality between separating volume/time also still exists at all.

Therefore, according to the invention a single opening time in s/min is not controlled, but this opening time is divided up in a plurality of sample taking cycles having corresponding short valve open times per cycle and so it will proceed that the respective opening time of the valve is merely varied in a limited range in which it is certain that the separating flow is proportional to the time. The actual control is carried out first and foremost in that the sample volume to be taken per minute is extracted in a number of cycles each having a short valve opening time per separating cycle whereby a cycle respectively consists of the valve opening time and the time the valve is not open per separating cycle. Thereafter, the number of separating cycles which the control is carried out with, can be determined from:

open time (s/min)=number of separating cycles (n/min)×valve open time per separating cycle (s)    (6)

Now, the number of possible separating cycles (n/min) which can be realized with a valve of the described type, is limited. Actually, the number of separating cycles in the upward direction of n=120 can easily be reached. For the reasons of wear and the high noise level, the number of separating cycles is however, preferably limited to n=30/min. Towards the lower limit, the number of separating cycles is likewise limited in that towards the end of milking where the milk flows are low, representative samples must still be extracted. This is particularly important since the milk content substance, in particular, the fat content of the milk, considerably changes towards the end of milking. The fat content towards the end of milking is considerably greater than at the start of milking. From this it follows, that the number of separating cycles should not fall below 2 to 3 per minute.

Should now the corresponding embodiment shown in FIG. 3 be measured with a constant hydrostatic pressure, it may not be possible, due to the large range of variations to be covered, to carry out a sufficient variation alone on the basis of the changes of the cycle count per minute with a constant valve separating time.

Furthermore, for the case when a boundary value for the cycle count per time is reached, the switching to shorter or longer valve opening times must then be carried out. For measurement at a constant hydrostatic pressure, the milk height produced by the hydrostatic pressure should not be so great in order to achieve a representative sample extraction with all kinds of milk flows (especially at the end of milking). With low hydrostatic pressure results in the separating flow being constant only over a narrow range of valve open time since here the influence from capillary and cohesion forces are of a particular significance. With the working under a constant, low hydrostatic pressure according to FIG. 3, it can therefore be necessary, in order to achieve a large range of valve opening times, to construct a calibration curve of separating volume per valve opening time which is then input in the processor for calculating the necessary valve open time per cycle.

The task to cover the total measurement range with a single sample extracting device can be carried out far more advantageously when the milk sample extracting device is operated in an arrangement according to FIG. 2 where the reservoir height is changed in dependence of the milk flow. In this case, it already results in a reduction of the ratio open time, maximum: minimum to merely 122:1, as can be taken from Table 3. That means, there already takes place a reducing of the measurement range by the respective milk flow which is already a reservoir height, that is, a hydrostatic pressure, and included therewith is the reduction of the respective opening times in dependence of the milk flow. In this case, the range of valve opening times per cycle can be limited respectively to a narrower range of around 0.1 to 0.8 seconds in which it is guaranteed that the separating flow is proportional to the time. As already discussed above, however, there also arises in this case the necessity that with small milk flows, which corresponds to a low reservoir height and respectively low hydrostatic pressure, a narrower valve open time period is chosen in order to ensure a proportionality between separating flow and opening time. As can be taken from Table 4,

TABLE 4

| Milk flow (ml/min) | Permitted number of separating cycle (n/min) (min. to max.) | Permitted opening time per separating cycle (s) (min. to max.) |
| --- | --- | --- |
| <250 | 2–4 | 0,10–0,25 |
| 800 | V | 0,10–0,60 |
| 1200 | V | 0,10–0,80 |
| V | V | V |
| >9000 | 10–30 | 0.10–≧2 | in dependence of the respective measured milk flow, different ranges of the number of separating cycles, as well as, the permitted valve open time per cycle are provided. For milk flows under 250 ml/min results in a minimum separating cycle number of 2 to 4 per minute while the permitted valve opening time per separating cycle lies between 0.1 and 0.25 seconds. The reason for this constricted valve opening time/cycle range is based on the fact that with longer valve opening times, the number of separating cycles and along with it also the piston effect of the valve, correspondingly decrease. Correspondingly greater ranges are produced for higher milk flows. The values of the valve openings time per separating cycle can be resolved by way of programming in steps of 0.02 seconds. If a change-over results from, for instance, a number of separating cycles reaching the boundary of its range due to a change of the, up till now, related valve opening times per separating cycle, the change-over takes place in such a way that the sample cycle time will increase and respectively decrease in the same relation as the valve opening time per separating cycle.

The respective control ranges, for instance, in accordance with Table 4, will first of all be inputted to the processor as range data. The calculation of the respective number of separating cycles for a fixed valve opening time per separating cycle is respectively calculated by the processor in dependence of the measured milk flow. In reaching a corresponding range boundary there takes place a corresponding change-over of the number of separating cycles in connection with a corresponding change of the valve opening time per separating cycle. Of course, such a change-over can also already take place before reaching the corresponding range boundary in order to possibly remain in an optimal relation of cycle number and valve opening time.

The above-stated tasks are only for the sake of example and apply respectively to an outlet cross-section of the through flow opening 31 and 131, of 0.0176 cm².

In the following, it should be shown also with the help of an example, how the number of separating cycles and the valve opening time per separating cycle is calculated and chosen:

The preset allowed value E (total milk amount) is 10,000 ml.

The desired total sample volume is 30 ml.

The measured instantaneous milk flow is 2500 ml/min.

From equation (1) a necessary separating volume per minute of 7.5 ml/min can be calculated. From equation (4) a separating flow (100%) as 61.15 ml/min can then be calculated.

From equation (5) the opening time as 27.36 S/min is then produced. From Table 4, with the assumed instantaneous milk flow, the number of separating cycles per minute can be calculated as 15. From this, the valve opening time per cycle is produced from equation (6) as 0.49 seconds per cycle. According to Table 4 this valve opening time per separating cycle is permitted.

The programme for controlling the sample extraction can still be further refined when it is considered that, for instance, with the milk flow measuring device shown in the drawings 2 to 5, that also the respective milk amounts which have already flowed are added up and therefore, the respective milk amount which has flowed in time intervals can be determined more exactly. Therefore, when in the milking stage the milk flow begins at first with the low value of around 200 ml/min, from this there would appear in such situations a cycle time of 30 seconds. Should the milk flow then increase relatively powerfully, the analysis sample which has been taken could be incorrect. Since with the known set-up a sample separation would first take place after 30 seconds, whereby it is assumed that in this time merely a milk volume of 100 ml has flowed, one can carry out a correction by a simultaneous steady measurement of the actual flowed milk amounts during the separating cycle and that a new adjustment of the cycle time of the valve opening time is requested when it is established by the measurement of the milk amount that already before the expiry of the cycle time of 30 seconds, around more than 100 ml of milk has flowed.

A control can also be provided of the type that determines a new cycle time or valve opening time when the change of the milk flow per time overshoots a predetermined threshold value.

A determination of the cycle time and the valve opening time can be carried out in the same way as the method to be carried out with the arrangements according to FIGS. 4 and 5. In this connection, there results merely a difference that the separating flow (100%) with a fully opened valve corresponds respectively to the flow through the ducts 241, 341. This separating flow (100%) is however, dependent on the relation of the cross-section of the entrance openings of these ducts to the ducts 226, 326 for transporting of the milk. Furthermore, this separating flow (100%) is dependent on the milk flow and is almost reproduceable but generally not proportional in its amount. The separating flow is best represented in the form of an empirically determined characteristic curve. The cleaning of the valve can be carried out with one of the cycle counts increased to a maximum.

I claim:

1. A device for extracting an analysis sample amount of milk from the milk flow milked from a cow, the analysis sample amount being proportional to the amount of milk which has been milked from the cow, whereby sample partial amounts are extracted from the milk flow dependent on the milk flow, comprising a fluid duct for transporting milk, a valve within said fluid duct, and a means for controlling said valve in cycles, each cycle including a valve opening time and a valve closing time, said valve opening time extracting said partial analysis sample amount, said controlling means having a means for storing a predetermined maximum of said analysis sample, a means for determining an expected total amount of milk to be milked from the particular cow based upon prior total amounts milked from the particular cow, and means for determining said valve opening time, said valve closing time, and a cycle time defined by said valve opening time and valve closing time, said cycle time and said valve opening time being determined to lie within a specified range of values, said controlling means determining one of said valve opening time and said cycle time dependent on the milk flow within said milk duct, and said determining means changing said valve opening time and cycle time in a ratio equal to values lying within said specified range.

2. The device according to claim 1, wherein said milk duct includes a chambers, said chamber stores milk therein at a build-up height, said sample flow opening being fluidly connected to said chamber.

3. The device according to claim 2, wherein devices for measuring milk build-up are provided in said chamber.

4. A milk sample extracting device for extracting a milk sample from milk flow milked from a cow, comprising a milk duct for transporting milk, a hollow housing connected in said milk duct, a milk flow measuring device positioned in said milk duct, a sample flow opening in said hollow housing, a valve assembly for selectively blocking and releasing said opening, an analysis sample container connected to said valve assembly for receiving the milk sample through said opening, and a processor means for controlling said valve assembly, said milk flow measuring device electrically communicating with said processor means, said valve assembly including an electrically controllable magnetic coil and a sealing body within said hollow housing moveable between a first position blocking said flow opening and a second position releasing said flow opening in response to an operation of said coil, and said processor means including a means for controlling a valve open time with said sealing body being in said second position and a cycle time of said sealing body dependent upon a measured value of milk flow from said milk flow rate measuring device, said controlling means keeping said valve open time and said cycle time within a range of values and changing said valve open time and said cycle time in a ratio equal to values within said range.

5. The device according to claim 4, wherein said sealing body is one of a permanent magnet material and a ferromagnetic material, and wherein one of a ferromagnetic body and a permanent magnet body for stopping the sealing body in said first position is disposed near said sample flow opening.

6. The device according to claim 5, wherein a pipe is formed by one of the ferromagnetic sealing body and the permanent magnet sealing body, said pipe forming an end of said sample flow opening creating a sample separating milk stream.

7. The device according to claim 5, wherein at least one of said sealing body and an end of said flow opening facing said sealing body has a layer of absorbing material.

8. The device according to claim 4, wherein said sealing body is a cylindrical body guided in lateral guide elements of said valve assembly.

9. The device according to claim 8, wherein said cylindrically shaped sealing body is moveable along a substantially cylindrical shaped guideway in said hollow housing, wherein recesses are provided in said guideway extending in a longitudinal direction of said sealing body, and said recesses for conducting the milk through said hollow housing are in communication with said sample flow opening when said sealing body is in said second position and are in communication with an end hollow housing facing said analysis sample container.

10. The device according to claim 9, wherein a connection between said sample flow opening and said recesses is substantially interrupted with an adjusting movement of said sealing body over a distance before reaching said first position closing said sample flow opening or respectively during an opening movement of said sealing body from said first position.

11. The device according to claim 4, wherein said magnetic coil is provided adjacent said second position of said sealing body.

12. The device according to claim 4, wherein said magnet coil is operable in an impulse mode.

13. The device according to claim 12, wherein said magnet coil is controllable respectively with the help of impulses of different current directing in said impulse mode for moving said sealing body between said first and second positions.

14. The device according to claim 13, wherein said impulses have a length between 10 and 100 msec.

15. The device according to claim 4, wherein said analysis sample holder is joined to said hollow housing at a connection, wherein a milking vacuum is connected to said milking duct to create a flow of milk therein, and wherein an auxiliary duct connects said milking vacuum to said connection of said analysis sample holder and said hollow housing creating a vacuum seal at said connection.

16. The device according to claim 15, wherein an end of said hollow housing is formed such that said analysis sample container is attachable in a seal-proof manner onto said end.

17. The device according to claim 4, wherein an end of said hollow housing facing said analysis sample container is formed as a pipe end insertable in a perforated covering of said analysis sample holder and said end of said hollow housing has a ring portion surrounding said pipe end, said ring portion being adapted to contact said covering of said analysis sample holder, wherein a vacuum device creates a vacuum to cause a milk flow in said milk duct, and wherein a circular space formed between an outside of said pipe end and said ring portion is connected to said vacuum device.

18. The device according to claim 4, wherein said milk duct includes a chamber and in said chamber milk is held at a predetermined build-up height, and wherein said sample flow opening is fluidly connected to said chamber.

19. The device according to claim 4, wherein said sample flow opening includes a sample extracting pipe projecting into said milk duct extending in a direction opposing milk flow in said milk duct.

20. The device according to claim 19, wherein said sample extracting pipe is positioned from an inside wall of said milk duct such that an axial center of an inlet opening of said sample extracting pipe is positioned at a distance generally at one third of a diameter of said milk duct.

21. The device according to claim 4, wherein a feedline for the milk connects said milk duct to said sample flow opening, said sample flow opening branches into a first duct and a second duct both extending through said hollow housing, a discharging duct being connected to an outlet opening of said first duct, said discharging duct being connected to said analysis sample container, said second duct being connected with a milk discharge duct, and wherein said sealing body is movable such that in said first position said outlet opening is closed and the second duct is released, and in said second position said outlet opening in said first duct is released and said second duct is closed.

* * * * *